United States Patent
Bae et al.

(10) Patent No.: US 10,179,903 B2
(45) Date of Patent: Jan. 15, 2019

(54) MICROORGANISM HAVING L-LYSINE PRODUCING ABILITY AND L-LYSINE PRODUCING METHOD USING SAME

(71) Applicant: CJ CHEILJEDANG CORPORATION, Seoul (KR)

(72) Inventors: Hyun Won Bae, Yongin-si (KR); Jun Ok Moon, Seoul (KR); Sung Ki Song, Bucheon-si (KR); Hyung Joon Kim, Seoul (KR); Hyo Jin Kim, Seoul (KR); Sang Jo Lim, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 6 days.

(21) Appl. No.: 15/302,738

(22) PCT Filed: Apr. 7, 2015

(86) PCT No.: PCT/KR2015/003478
§ 371 (c)(1),
(2) Date: Jun. 14, 2017

(87) PCT Pub. No.: WO2015/156583
PCT Pub. Date: Oct. 15, 2015

(65) Prior Publication Data
US 2018/0135031 A1    May 17, 2018

(30) Foreign Application Priority Data

Apr. 9, 2014    (KR) .................. 10-2014-0042397

(51) Int. Cl.
| | |
|---|---|
| *C12N 1/20* | (2006.01) |
| *C12N 9/12* | (2006.01) |
| *C12P 13/08* | (2006.01) |
| *C12N 9/10* | (2006.01) |
| *C12N 15/77* | (2006.01) |

(52) U.S. Cl.
CPC ......... *C12N 9/1217* (2013.01); *C12N 9/1029* (2013.01); *C12N 15/77* (2013.01); *C12P 13/08* (2013.01); *C12Y 203/01008* (2013.01); *C12Y 207/02001* (2013.01)

(58) Field of Classification Search
CPC .................................. C12N 1/20; C12P 13/08
USPC ............................................... 435/145, 252.3
See application file for complete search history.

(56) References Cited

U.S. PATENT DOCUMENTS

| 7,833,762 B2 | 11/2010 | Kataoka et al. |
|---|---|---|
| 2003/0124688 A1 | 7/2003 | Kim et al. |
| 2010/0143984 A1 | 6/2010 | Park et al. |
| 2010/0317067 A1 | 12/2010 | Kim et al. |
| 2010/0330624 A1 | 12/2010 | Jang et al. |

FOREIGN PATENT DOCUMENTS

| JP | 2007-222163 A | 9/2007 |
|---|---|---|
| JP | 2009-60791 A | 3/2009 |
| KR | 10-1994-0001307 B1 | 2/1994 |
| KR | 10-0159812 B1 | 11/1998 |
| KR | 10-0397322 B1 | 9/2003 |
| KR | 10-0924065 B1 | 10/2009 |
| KR | 10-0930203 B1 | 12/2009 |
| KR | 10-1126041 B1 | 3/2012 |
| WO | WO 2007/086608 A1 | 8/2007 |
| WO | WO 2007/116955 A2 | 10/2007 |

OTHER PUBLICATIONS

PCT/KR2015/003478.written opinion PCT.ISA.237. dated Jan. 2015.*
Gerstmeir et al., "Acetate metabolism and its regulation in *Corynebacterium glutamicum*," *Journal of Biotechnology* 104:99/122, 2003.
UniProtKB-P77845 (ACKA_CORGL) (5 pages) (Feb. 1, 1997).
UniProtKB-P27550 (ACSA_ECOLI) (6 pages) (Oct. 1, 1993).
Binder et al. "A high-throughput approach to identify genomic variants of bacterial metabolite producers at the single-cell level," *Genome Biology* 13:R40 (12 pages) (2012).
Ebbighausen et al., "Carrier-mediated acetate uptake in *Corynebacterium glutamicum*," *Archives of Microbiology* 155:505-510 (1991).
Lin et al., "Acetyl-CoA synthetase overexpression in *Escherichia coli* demonstrates more efficient acetate assimilation and lower acetate accumulation: a potential tool in metabolic engineering," *Appl. Microbiol. Biotechnol.* 71:870-874 (2006).
Reinscheid et al., "Cloning, sequence analysis, expression and inactivation of the *Corynebacterium glutamicum* pta-ack operon encoding phosphotransacetylase and acetate kinase," *Microbiology* 145:503-513 (1999).
NCBI Reference Sequence: WP_003862874.1 (May 7, 2013).
NCBI Reference Sequence: WP_011015350.1 (May 15, 2013).
NCBI Reference Sequence: WP_000078239.1 (Aug. 28, 2013).

* cited by examiner

*Primary Examiner* — Tekchand Saidha
(74) *Attorney, Agent, or Firm* — Seed IP Law Group LLP (57) ABSTRACT

The present invention relates to a microorganism having improved L-lysine-producing ability and an L-lysine-producing method using the same. More specifically, the present invention relates to a microorganism of the genus of *Corynebacterium*, in which acetate kinase activity is further enhanced over inherent activity, and an L-lysine-producing method using the same.

6 Claims, 2 Drawing Sheets

Specification includes a Sequence Listing.

[FIG. 1a]

Comparison of growth in media without acetate

[FIG. 1b]

Comparison of growth in media containing acetate

MICROORGANISM HAVING L-LYSINE PRODUCING ABILITY AND L-LYSINE PRODUCING METHOD USING SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_427USPC_SEQUENCE_LISTING.txt. The text file is 20 KB, was created on Jan. 23, 2017, and is being submitted electronically via EFS-Web.

TECHNICAL FIELD

The present disclosure relates to a microorganism producing L-lysine and a method for producing L-lysine using the microorganism.

BACKGROUND ART

A microorganism of the genus *Corynebacterium* can utilize organic acids such as gluconate, acetate, and pyruvate, as well as glucose, sucrose, and fructose, as a carbon source. Among these, acetate, which is an organic acid belonging to monocarboxylic acids, is introduced into cells by passive diffusion or monocarboxylic acid transporter (MctC) when utilized by a microorganism of the genus *Corynebacterium*, phosphorylated by acetate kinase (ackA) to be converted into acetyl phosphate, and formed into acetyl-CoA by phosphotransacetylase (pta). The thus-formed acetyl-CoA is immediately introduced into the tricarboxylic acid (TCA) cycle and glyoxylate cycle (*J. Bacteriol.* 2009. 191: 940-948), and thereby oxaloacetate, which is a precursor of lysine, is formed.

However, when a strain of the genus *Corynebacterium* is cultured using acetate as a sole or mixed carbon source, there is a problem in that a growth inhibition phenomenon may occur according to its concentration. Acetate has been known to have limitations in that its metabolic rate is low compared to that of saccharides such as glucose, and also, since acetate can inhibit cell growth when it is present in a certain concentration in a cell, the increase of acetate concentration in a culture medium can increase the lag phase, thereby delaying the entire culture time (*Arch. Microbiol.* 1991. 155: 505-510). Accordingly, there is a need for the development of a method for rapidly converting the acetate in a culture medium into acetyl-CoA in a cell.

However, acetate kinase and phosphotransacetylase, which are used in the pathway of acetate activation, have a bidirectionality (a reversible reaction) and thus there is a problem in that acetyl-CoA may be converted again into acetate, and there is also a report that these may have a negative effect on the production of L-lysine. Therefore, the development of a method for effectively utilizing acetate still remains inactive.

DISCLOSURE

Technical Problem

The present inventors have made many efforts to develop a microorganism for the efficient utilization of acetate, which is produced during the fermentation process or provided as a new carbon source, and as a result, they have confirmed that a microorganism with an activity of enhanced acetate kinase on the pathway of acetate activation can increase the ability to utilize acetate and produce L-lysine, thereby completing the present invention.

Technical Solution

An object of the present disclosure is to provide a microorganism of the genus *Corynebacterium* producing L-lysine, in which an activity of acetate kinase is enhanced compared to its endogenous activity.

Another object of the present disclosure is to provide a method for producing L-lysine using the above microorganism.

Advantageous Effects of the Invention

The microorganism according to the present disclosure, being a strain having an increased acetate-utilizing ability due to an enhanced pathway of acetate activation, is a microorganism that can produce L-lysine in high yield. The thus-prepared L-lysine can be used in various products including not only animal feeds or animal feed additives but also human foods or food additives, drugs, etc.

BEST MODE

An aspect of the present disclosure provides a microorganism of the genus *Corynebacterium* producing L-lysine, in which an activity of acetate kinase is enhanced. Specifically, the microorganism is a microorganism of the genus *Corynebacterium* producing L-lysine, in which an activity of acetate kinase is enhanced compared to its endogenous activity.

As used herein, the term "L-lysine" refers to a kind of L-amino acid, which is a basic a-amino acid and an essential amino acid not synthesized in vivo, having a chemical formula of $NH_2(CH_2)_4CH(NH_2)COOH$.

Acetate is an organic acid belonging to monocarboxylic acids, which is introduced into cells by passive diffusion or monocarboxylic acid transporter when utilized by a microorganism of the genus *Corynebacterium*, phosphorylated by acetate kinase to be converted into acetyl phosphate, and formed into acetyl-CoA by phosphotransacetylase. The thus-formed acetyl-CoA is immediately introduced into the tricarboxylic acid (TCA) cycle and glyoxylate cycle, and thereby oxaloacetate, a lysine precursor, is formed. Acetate can be used as a carbon source in a microorganism of the genus *Corynebacterium*. However, when the microorganism is cultured using acetate as a sole or mixed carbon source, there is a problem in that growth inhibition phenomenon occurs according to the concentration (*Arch. Microbiol.* 1991. 155: 505-510).

Broadly, there are two pathways for activating acetate to convert acetate to acetyl-CoA in a cell. As described above, two enzymes (i.e., acetate kinase and phosphotransacetylase) sequentially act in a strain of the genus *Corynebacterium*. A gene, ackA, is known to encode acetate kinase and a gene, pta, is known to encode phosphotransacetylase (*Microbiol.* 1999 145: 503-513). In another pathway, acetyl-CoA synthetase is involved in a strain of the genus *Escherichia* and a gene, acs, is known to encode acetyl-CoA synthetase (*Appl Microbiol Biotechnol.* 2006. 71: 870-874). However, since the activation pathway in the strain of the genus *Escherichia* is due to a reversible reaction, there has been no attempt to simply enhance the pathway.

Surprisingly, however, the present inventors have confirmed not only that the enhancement of acetate kinase can rapidly convert acetate into acetyl-CoA in a cell, but also that the drawback of growth inhibition described above can be overcome to increase the L-amino acid-producing ability. Therefore, the present inventors were able to provide a novel microorganism of the genus *Corynebacterium* producing L-lysine, in which an activity of acetate kinase is enhanced compared to its endogenous activity.

In an exemplary embodiment of the present disclosure, it was confirmed that a microorganism in which an activity of the ackA gene was enhanced showed a rapid consumption rate of acetate and also a significant reduction in the lag phase in the growth of the microorganism. In contrast, it was confirmed that when an activity of pta gene was enhanced, the microorganism did not show any significant difference in the rate of acetate consumption compared to that of the control group (FIGS. 1a and 1b), and thus it was confirmed that the protein important for increasing acetate-utilizing ability by acetate activation and increasing the L-lysine-producing ability without growth inhibition is acetate kinase. That is, it was confirmed that a microorganism which can produce L-lysine in high yield and has an increased acetate-utilizing ability without growth inhibition can be prepared by enhancing the activity of acetate kinase using various known methods based on the above results.

The microorganism of the genus *Corynebacterium* of the present disclosure, which has increased acetate-utilizing ability and increased L-lysine-producing ability, may be a microorganism of the genus *Corynebacterium* which can produce L-lysine and has an enhanced acetate kinase activity compared to its endogenous activity.

Additionally, the microorganism of the genus *Corynebacterium* which has increased acetate-utilizing ability and increased L-lysine-producing ability may be a microorganism of the genus *Corynebacterium* having an enhanced acetate kinase activity compared to its endogenous activity, in which, additionally, (i) an activity of phosphotransacetylase is enhanced compared to its endogenous activity; (ii) an activity of acetyl-CoA synthetase is introduced or enhanced; or (iii) an activity of phosphotransacetylase is enhanced compared to its endogenous activity and an activity of acetyl-CoA synthetase is introduced or enhanced.

The present inventors have confirmed that, in a microorganism having an activity of acetate kinase, which is most important for increasing acetate-utilizing ability and L-lysine-producing ability, enhanced compared to its endogenous activity, when an activity of phosphotransacetylase is additionally enhanced compared to its endogenous activity and/or an activity of acetyl-CoA synthetase is additionally introduced or enhanced, the acetate-utilizing ability is further increased, and the present inventors provide the novel microorganism in the present disclosure. In an exemplary embodiment of the present disclosure, it was confirmed that further introduction of acs gene, which is derived from a microorganism of the genus *Escherichia* and encodes acetyl-CoA, can increase the rate of acetate consumption (FIG. 3), and the result suggests that introduction or enhancement of the activity of acetyl-CoA synthetase may also increase the rate of acetate consumption, thereby increasing L-lysine-producing ability.

As used herein, the term "acetate kinase (EC 2.7.2.1)" refers to an enzyme which has the function of producing acetyl phosphate by phosphorylating acetate. The genes encoding the acetate kinase may be collectively referred to as ackA, and the protein and gene sequences of the acetate kinase may be obtained from a known database (e.g., GenBank of NCBI), but are not limited thereto. The acetate kinase may have an amino acid sequence of SEQ ID NO: 12 but any protein sequence having the activity of acetate kinase may be included without limitation.

As used herein, the term "phosphotransacetylase (EC 2.3.1.8)" refers to an enzyme which has the function of converting acetyl phosphate into acetyl-CoA by the reaction shown below.

CoA+acetyl phosphate↔acetyl-CoA+phosphate

As used herein, the term "phosphotransacetylase" may be used interchangeably with enzymes such as phosphate acetyltransferase and phosphoacylase. The gene encoding the phosphotransacetylase may be collectively referred to as pta, and the protein and gene sequences of the phosphotransacetylase may be obtained from a known database (e.g., GenBank of NCBI), but are not limited thereto. The phosphotransacetylase may have an amino acid sequence of SEQ ID NO: 13, but any protein sequence having the activity of phosphotransacetylase may be included without limitation.

As used herein, the term "acetyl-CoA synthetase (EC 6.2.1.1)" refers to an enzyme which has the function of converting acetate into acetyl-CoA by the reaction shown below.

acetate+CoA↔acetyl-CoA

The gene encoding the acetyl-CoA synthetase may be collectively referred to as acs, and the protein and gene sequences of the acetyl-CoA synthetase may be obtained from a known database (e.g., GenBank of NCBI), but are not limited thereto. The acetyl-CoA synthetase may have an amino acid sequence of SEQ ID NO: 14, but any protein sequence having the activity of acetyl-CoA synthetase may be included without limitation.

Each of the proteins described above may include without limitation, in addition to the amino acid sequences represented by SEQ ID NOS, any amino acid sequence which has a homology of 80% or higher, specifically 90% or higher, more specifically 95% or higher, and even more specifically 97% or higher, to the above-listed amino acid sequences, as long as the amino acid sequences encode proteins which have an effect substantially the same as or corresponding to each of the proteins. Additionally, it is obvious that any modified protein having the homology described above can belong to the scope of the present disclosure, although the protein may have an amino acid sequence with a partial deletion, modification, substitution, or addition therein.

Additionally, the genes encoding each of the proteins of the present disclosure may also include without limitation, in addition to the polynucleotide sequences described by SEQ ID NOS, any gene sequence encoding the proteins, which has a homology of 80% or higher, specifically 90% or higher, more specifically 95% or higher, even more specifically 98% or higher, and most specifically 99% or higher, to each of the above-listed polynucleotide sequences, as long as the gene sequence encodes a protein which has an effect substantially the same as or corresponding to each of the proteins. Additionally, it is obvious that any polynucleotide sequence having the above homologies can belong to the scope of the present disclosure, although the sequence may have a partial deletion, modification, substitution, or addition therein.

As used herein, the term "homology" refers to a degree of identity between polypeptide sequences or amino acid sequences encoding proteins, and when there is a sufficiently high percentage of homology, the expression products of corresponding genes may have the same or similar activities.

As used herein, the term "endogenous activity" refers to an active state of a polypeptide in a microorganism in a non-modified state, i.e., in a natural state.

As used herein, the term "enhancement of an activity of a protein compared to its endogenous activity" refers to increasing the intracellular activity of a protein in a microorganism by modifying the protein to improve the intracellular activity compared to the activity of the protein possessed in its natural state. Additionally, as used herein, the term "enhancement of an activity of a protein" refers to not only the enhancement of the activity of a protein compared to its endogenous activity, but also the increase of the intracellular activity of a particular protein by modifying a microorganism which did not possess the activity of the particular protein originally to have the activity of the particular protein and modifying to improve its intracellular activity.

The "enhancement" not only includes the drawing of a higher effect than the original function due to the increase in the activity of the protein itself, but it may be performed by at least one method selected from the group consisting of a method for increasing the copy number of a polynucleotide encoding the protein, a method for introducing a modification in the regulatory sequence of a gene encoding the protein, a method for substituting the regulatory sequence of a gene encoding the protein on the chromosome with a sequence having strong activity, a method for substituting the gene encoding the protein with a mutated gene to increase the activity of the protein, and a method for introducing a modification in the gene encoding the protein on the chromosome to enhance the activity of the protein, but any known method which can enhance the activity of the protein compared to its endogenous activity or enhance the introduced activity may be included without limitation.

As used herein, the term "introduction of an activity of a protein" refers to providing an activity of a particular protein to a microorganism which does not have the activity of the particular protein.

The "introduction of an activity of a protein" may be performed in various methods known in the art, for example: a method for inserting a polynucleotide including a polynucleotide sequence encoding the protein into the chromosome; a method for increasing the copy number of a polynucleotide by a method such as introducing the polynucleotide to a microorganism via an introduction into a vector system; a method for introducing a promoter capable of exhibiting improved activity or introducing the protein with a modification in the promoter into an upstream region of the polynucleotide sequence encoding the protein; a method for introducing a modification into the polynucleotide sequence encoding the protein; etc., but any known method that can introduce an activity of a protein may be included without limitation.

In the above, the increase of copy number of a polynucleotide may be performed in a form in which the polynucleotide is operably linked to a vector, or by inserting the polynucleotide into the chromosome of a host cell, although the method is not particularly limited thereto. Specifically, the increase of copy number of a polynucleotide may be performed by introducing a vector which can replicate and function regardless of a host cell and to which the polynucleotide encoding the protein of the present disclosure is operably linked; or may be performed by introducing a vector into a host cell, which can insert the polynucleotide into the chromosome of the host cell and to which the polynucleotide is operably linked.

The vector is a DNA construct including the polynucleotide sequence of a polynucleotide encoding a target protein, which is operably linked to an appropriate regulatory sequence to enable the expression of the target protein in a host cell. The regulatory sequence includes a promoter capable of initiating transcription, any operator sequence for the regulation of the transcription, a sequence encoding an appropriate mRNA ribosome-binding domain, and a sequence regulating the termination of transcription and translation. The vector, after being transformed into an appropriate host cell, may be replicated or function regardless of the host genome, or may be integrated into the host genome itself.

The vector used in the present disclosure may not be particularly limited as long as the vector is replicable in the host cell, and it may be constructed using any vector known in the art. Examples of the vector may include natural or recombinant plasmids, cosmids, viruses, and bacteriophages. For example, as a phage vector or a cosmid vector, pWE15, M13, λMBL3, λMBL4, λIXII, λASHII, λAPII, λt10, λt11, Charon4A, Charon21A, etc. may be used; and as a plasmid vector, those based on pBR, pUC, pBluescriptII, pGEM, pTZ, pCL, pET, etc. may be used. The vectors that can be used in the present disclosure are not particularly limited but any known expression vector, e.g., pDZ, pACYC177, pACYC184, pCL, pECCG117, pUC19, pBR322, pMW118, pCC1BAC vector, etc., may be used.

Additionally, the polynucleotide encoding the endogenous target protein may be replaced with a modified polynucleotide within the chromosome by a vector for the insertion of a chromosome within the host cell. Alternatively, the polynucleotide encoding a foreign target protein to be introduced into the chromosome may be replaced with a modified polynucleotide. The insertion of the polynucleotide into the chromosome may be performed using any known method in the art, for example, by homologous recombination. Since the vector of the present disclosure can be inserted into the chromosome via homologous recombination, a selection marker for the confirmation of the insertion into the chromosome may be further included. The selection marker is used for the selection of a transformed cell, i.e., to confirm whether the target polynucleotide has been inserted, and markers capable of providing selectable phenotypes such as drug resistance, nutrient requirement, resistance to cytotoxic agents, and expression of surface proteins may be used. Under the circumstances where selective agents are treated, only the cells capable of expressing the selection markers can survive or express other phenotypic traits, and thus the transformed cells can be selected.

As used herein, the term "transformation" refers to a process of introducing a vector including a polynucleotide encoding a target protein into a host cell, thereby enabling the expression of the polynucleotide encoded by the protein in the host cell. For the transformed polynucleotide, it does not matter whether it is inserted into the chromosome of a host cell and located therein or located outside the chromosome, as long as it can be expressed in the host cell. Additionally, the polynucleotide includes DNA and RNA which encode the target protein. The polynucleotide may be inserted in any form as long as it can be introduced into a host cell and expressed therein. For example, the polynucleotide may be introduced into a host cell in the form of an expression cassette, which is a gene construct including all essential elements required for self-expression. The expression cassette may conventionally include a promoter operably connected to the polynucleotide, a transcription termination signal, a ribosome-binding domain, and a translation termination signal. The expression cassette may be in the form of an expression vector capable of self-replication. Additionally, the polynucleotide may be introduced into a host cell as it is and operably connected to a sequence essential for its expression in the host cell.

Additionally, as used herein, the term "operably connected" refers to a functional connection between a promoter sequence, which initiates and mediates the transcription of the polynucleotide encoding the target protein of the present disclosure, and the above gene sequence.

The method for transforming a vector of the present disclosure may include any method which can introduce a polynucleotide into a cell, and the transformation may be performed by selecting an appropriate technique known in the art according to the host cell. For example, the method may include electroporation, calcium phosphate ($CaPO_4$) precipitation, calcium chloride ($CaCl_2$) precipitation, microinjection, a polyethylene glycol (PEG) method, a DEAE-dextran method, a cationic liposome method, and a lithium acetate/DMSO method, etc., but is not limited thereto.

the host cell to be used would be better to have high efficiency of DNA introduction and high expression efficiency of the introduced DNA, and for the purpose of the present disclosure, the host cell may be a microorganism of the genus *Corynebacterium*.

Then, the introduction of a modification in the expression control sequence for increasing the expression of a polynucleotide, although not particularly limited thereto, may be performed by inducing a modification in the polynucleotide sequence via deletion, insertion, conservative substitution or non-conservative substitution, or a combination thereof in order to further enhance the activity of the expression control sequence; or by replacing the polynucleotide sequence with a polynucleotide sequence with enhanced activity. The expression control sequence, although not particularly limited thereto, may include a promoter, an operator sequence, a sequence encoding a ribosome-binding domain, a sequence for regulating termination of transcription and translation, etc.

A strong exogenous promoter, instead of the original promoter, may be connected to the upstream region of the expression unit of the polynucleotide. Examples of the strong exogenous promoter may include pcj7 promoter, lysCP1 promoter, EF-Tu promoter, groEL promoter, aceA promoter, aceB promoter, etc., and preferably, a promoter derived from *Corynebacterium* such as pcj7 promoter or lysCP1 promoter. The sequence of lysCP1 promoter and a method for its preparation are described in Korean Patent No. 10-0930203, and the entirety of the above Korean patent is included herein as a reference example. In an exemplary embodiment of the present disclosure, it was confirmed that the linking of the ackA gene to the lysCP1 promoter, which is a strong promoter, resulted in improved acetate-utilizing ability compared to that of the control group (FIG. 3), and the result suggests that as the amount of ackA gene expression increases the rate of acetate utilization increases.

Furthermore, the modification of a polynucleotide sequence on the chromosome may be performed by inducing a modification on the expression control sequence via deletion, insertion, non-conservative or conservative substitution, or a combination thereof for further enhancing the activity of the polynucleotide sequence; or by replacing with an improved polynucleotide sequence for providing stronger activity.

Generally, the introduction or enhancement of the activity of a protein may increase the activity or concentration of the corresponding protein relative to the activity or concentration of a wild-type protein or in a microorganism strain at the initial stage from at least 10%, 25%, 50%, 75%, 100%, 150%, 200%, 300%, 400%, or 500%, to a maximum of 1000% or 2000%, but is not limited thereto.

As used herein, the term "a microorganism producing L-lysine" refers to a microorganism strain that can produce L-lysine for the purpose of the present disclosure, and it is a strain that can efficiently utilize acetate in the culture medium and accumulate L-acetate without growth inhibition. The microorganism may include all microorganisms of the genus *Corynebacterium* having an enhanced activity of acetate kinase compared to its endogenous activity, for example, *Corynebacterium glutamicum*, *Corynebacterium ammoniagenes*, *Corynebacterium thermoaminogenes*, *Brevibacterium flavum*, *Brevibacterium fermentum*, etc., but is not limited thereto. In an exemplary embodiment, the microorganism of the genus *Corynebacterium* may be *Corynebacterium glutamicum*, and examples of *Corynebacterium glutamicum* may include KCCM11016P (Korean Patent No. 10-0397322), KCCM10770P (Korean Patent No. 10-0924065), KCCM11347P (Korean Patent No. 10-0073610), and CJ3P (Binder et al. *Genome Biology* 2012, 13: R40), but are not limited thereto.

In an exemplary embodiment of the present disclosure, it was confirmed that when the ackA gene was overexpressed in *Corynebacterium glutamicum* KCCM11016P used as the parent strain of the representative microorganism of the genus *Corynebacterium*, the acetate-utilizing ability was increased and the amount of L-lysine production was increased without growth inhibition (Examples 2 to 6). Furthermore, the overexpression of ackA gene in various microorganisms of the genus *Corynebacterium* (KCCM10770P, KCCM11347P, or CJ3P) also showed an increase in their ability to produce L-lysine (Example 7), and the result suggests that the ability to produce L-lysine is increased by the enhancement of the protein activity in the microorganism of the genus *Corynebacterium*, in which the acetate kinase encoded by the ackA gene is used in acetate utilization. Additionally, it was confirmed that further addition of phosphotransacetylase activity and/or introduction or enhancement of acetyl-CoA activity, in addition to the enhancement of the activity of acetate kinase, encoded by the ackA gene, can also increase the acetate-utilizing ability and the L-lysine-producing ability.

Another aspect of the present disclosure provides a method for producing L-lysine, including: (i) culturing the novel microorganism of the genus *Corynebacterium* having increased L-lysine-producing ability due to increased acetate-utilizing ability in a medium; and (ii) recovering L-lysine from the cultured medium or the cultured microorganism.

The microorganism of the genus *Corynebacterium* having increased L-lysine-producing ability is the same as described above.

As used herein, the term "culture" refers to growing a microorganism under appropriately and artificially controlled environmental conditions. In the present disclosure, the process of obtaining L-lysine by culturing the microorganism of the genus *Corynebacterium* may be performed using the methods well known in the art. Specifically, the culture may be performed continuously in a batch process (fed batch or repeated fed batch process), but is not limited thereto.

The medium used in the culture must appropriately satisfy the requirements for specific strains. The culture medium for *Corynebacterium* strains is already known (e.g., *Manual of Methods for General Bacteriology. American Society for Bacteriology*. Washington D.C., USA, 1981). Examples of the carbon sources to be used in the medium may include sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as gluconic acid, acetic acid, and pyruvic acid, but are not limited thereto. These carbon sources may be used alone or in combination. Examples of the nitrogen sources to be used in the medium may include peptone, yeast extract, meat gravy, malt extract, corn steep liquor, soybean flour, and urea; or inorganic compounds such as ammonium sulfate, ammonium chloride, ammonium phosphate, ammonium carbonate, and ammonium nitrate. These nitrogen sources may also be used alone or in combination. Examples of the phosphorus sources to be used in the medium may include potassium dihydrogen phosphate, dipotassium hydrogen phosphate, or corresponding sodium-containing salts. Additionally, metal salts such as magnesium sulfate or iron sulfate required for growth may be contained in the medium. Lastly, essential materials for growth, such as amino acids and vitamins, may also be contained in addition to the materials described above. Additionally, precursors suitable for a culture medium may be used. These sources may be added to a culture in an appropriate manner during the culture by a batch culture or a continuous culture. These various methods are disclosed in references (e.g., "*Biochemical Engineering*" by James M. Lee, Prentice-Hall International Editions, 138-176).

The pH of a culture may be adjusted by appropriately using a compound such as sodium hydroxide, potassium hydroxide, and ammonia, or an acid such as phosphoric acid and sulfuric acid. Additionally, an antifoaming agent such as a fatty acid polyglycol ester may be used to prevent foam generation. Additionally, for maintaining the aerobic state of the culture, oxygen or an oxygen-containing gas (e.g., air) may be injected into the culture. The culture temperature may normally be from 20° C. to 45° C., specifically, from 25° C. to 40° C., but may vary according to the conditions. Additionally, the culture may be continued until the maximum amount of the desired L-amino acid is obtained, which may be achieved in 10 hours to 100 hours. L-lysine may be secreted into a culture medium or may be contained in cells.

The method for producing L-lysine of the present disclosure may include recovering lysine from the cultured microorganism or the cultured medium. The method for recovering L-lysine from the cultured microorganism or the cultured medium may be performed using a method known in the art, e.g., centrifugation, filtration, anion exchange chromatography, crystallization, HPLC, etc.), but the method is not limited thereto.

The recovering may include a purification process.

DETAILED DESCRIPTION OF THE INVENTION

Hereinafter, the present invention will be described in more detail with reference to the following examples and experimental examples. However, the following examples and experimental examples are provided for illustrative purposes only, and the scope of the present invention should not be limited thereto in any manner.

Example 1

Preparation of a Vector for Inserting ackA, pta, or pta and ackA on Chromosome

In order to prepare a vector for independently or simultaneously further inserting ackA gene and pta gene on the chromosome of *Corynebacterium*, pDZTN vector (Korean Patent No. 10-1126041) designed from pDZ vector was used as the basic vector for the insertion of target genes into the transposon region. Since the two genes establish an operon in the form of pta-ackA, for the sole overexpression of the ackA gene for further insertion, the promoter region of the pta-ackA operon was operably linked to the upstream region of the open-reading frame (ORF) of the ackA gene. The primer sequences used in Examples are shown in Table 1 below.

For the preparation of a vector for further insertion of the ackA gene, primers (SEQ ID NOS: 1 and 2) for amplifying the ackA gene were synthesized based on the polynucleotide sequences reported previously, and the ORF region of the ackA gene with a size of about 1300 bp was amplified by PCR using the chromosome of *Corynebacterium glutamicum* ATCC 13032 as a template. In particular, PCR was performed under the following conditions: denaturation at 94° C. for 5 min; 30 cycles of denaturation at 94° C. for 30 sec, annealing at 56° C. for 30 sec, and polymerization at 72° C. for 90 sec; and polymerization at 72° C. for 7 min. The underlined parts on the polynucleotide sequences represent the restriction sites.

TABLE 1

| Primer | Sequence | SEQ ID NO |
|---|---|---|
| ackA primer 1 | atcgcatatggcattggcacttgttttg | 1 |
| ackA primer 2 | atcgactagtatccgtgcagtttcaccccttaaa | 2 |
| Ppta primer 1 | atcgactagtctttgctggggtcagatttgtcac | 3 |
| Ppta primer 2 | atcgcatatgtcgcctttctaatttcagcct | 4 |
| pta primer | atcgactagtggcagagttttcggggttgac | 5 |

Furthermore, primers (SEQ ID NOS: 3 and 4) for amplifying the promoter region of the pta-ackA operon were synthesized and a promoter region with a size of about 350 bp was amplified by PCR using the chromosomal DNA of *Corynebacterium glutamicum* ATCC 13032 as a template. In particular, PCR was performed under the following conditions: denaturation at 94° C. for 5 min; 30 cycles of denaturation at 94° C. for 30 sec, annealing at 56° C. for 30 sec, and polymerization at 72° C. for 90 sec; and polymerization at 72° C. for 7 min. The underlined parts in the polynucleotide sequences represent the restriction sites.

The PCR-amplified DNA fragments were treated with restriction enzymes, SpeI and NdeI, to obtain DNA segments, respectively. The thus-obtained DNA segments were ligated into pDZTN vector having a SpeI end, transformed into *E. coli* DH5α, and plated on LB solid medium containing kanamycin (25 mg/L). The colonies transformed with the vector, in which a target gene was inserted, were selected, the plasmid was obtained by the conventionally known plasmid extraction method, and the thus-obtained plasmid was named as pDZTN-Ppta_ackA.

For the preparation of a vector for further insertion of the pta gene, a primer (SEQ ID NO: 5) at the ORF end region of the pta gene was synthesized, and the pta gene region with a size of about 1750 bp was amplified by PCR using the chromosome of *Corynebacterium glutamicum* ATCC 13032 as a template along with primers (SEQ ID NOS: 3 and 5) for the amplification of the region spanning from the promoter to the ORF end of the pta gene. In particular, PCR was performed under the following conditions: denaturation at 94° C. for 5 min; 30 cycles of denaturation at 94° C. for 30 sec, annealing at 56° C. for 30 sec, and polymerization at 72° C. for 90 sec; and polymerization at 72° C. for 7 min.

The PCR-amplified DNA fragments were treated with a restriction enzyme, SpeI, to obtain DNA segments. The thus-obtained DNA segments were ligated into pDZTN vector having a SpeI end to obtain a plasmid and the plasmid was named as pDZTN-pta.

For the preparation of a vector for simultaneous insertion of the two genes in the form of an operon, the pta-ackA gene region with a size of about 3000 bp was obtained by PCR using the chromosome of *Corynebacterium glutamicum* ATCC 13032 as a template along with primers (SEQ ID NOS: 3 and 2), which are for amplifying the region spanning from the predicted promoter region of the pta-ackA gene operon (SEQ ID NO: 10) to the ORF end of the ackA gene. In particular, PCR was performed under the following conditions: denaturation at 94° C. for 5 min; 30 cycles of denaturation at 94° C. for 30 sec, annealing at 56° C. for 30 sec, and polymerization at 72° C. for 3 min; and polymerization at 72° C. for 7 min. The PCR-amplified DNA fragments were treated with a restriction enzyme, SpeI, to obtain DNA segments. The thus-obtained DNA segments were ligated into pDZTN vector having a SpeI end to obtain a plasmid and the plasmid was named as pDZTN-pta-ackA.

Example 2

Analysis of Acetate-utilizing Ability of the Strain with Inserted ackA and/or pta Gene on Chromosome The three kinds of vectors prepared in Example 1, i.e., pDZTN-Ppta_ackA, pDZTN-pta, and pDZTN-pta-ackA, were transformed into *Corynebacterium glutamicum* KCCM11016P (the microorganism was originally disclosed as KFCC10881, re-deposited to an international depositary authority under the Budapest Treaty and assigned the Accession No. KCCM11016P; Korean Patent Nos. 10-0159812 and 10-0397322) by electric pulse method, and the strains, in which target genes were inserted on the chromosome by homologous recombination, were selectively isolated by PCR and named as KCCM11016P::Ppta_ackA(Tn), KCCM11016P::pta(Tn), and KCCM11016P::pta-ackA(Tn).

Figure 1A:
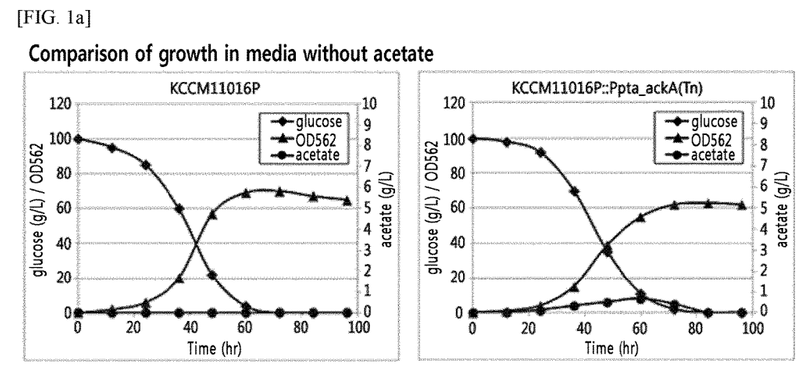
FIGS. 1a and 1b show graphs illustrating the analysis of acetate-utilizing abilities of KCCM11016P (a control strain) and a modified KCCM11016P (a modified strain introduced with pta and pta-ackA), in a medium with acetate (FIG. 1a) and in a medium without acetate (FIG. 1b).
Figure 1B:
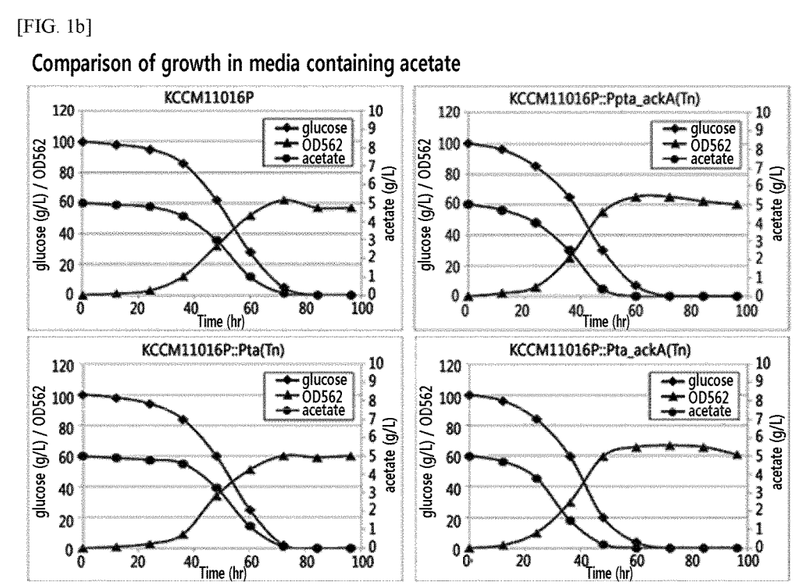

The three kinds of strains and the control group were inoculated into a 250 mL corner-baffle flask containing 25 mL of a seed culture medium, and cultured with shaking at 200 rpm at 30° C. for 20 hours. Then, 1 mL of the seed culture solution was inoculated into a 250 mL corner-baffle flask containing 24 mL of a production medium, and cultured with shaking at 200 rpm at 37° C. for 96 hours. The cultured medium was collected every 12 hours during the culture and the amount of glucose and acetate remaining in the cultured medium and the absorbance at 562 nm were analyzed, and the results are shown in FIGS. 1*a* and 1*b*.

<Seed Culture Medium (pH 7.0)>

Glucose (20 g), $(NH_4)_2SO_4$ (10 g), Peptone (10 g), Yeast Extract (5 g), Urea (1.5 g), $KH_2PO_4$ (4 g), $K_2HPO_4$ (8 g), $MgSO_4 \cdot 7H_2O$ (0.5 g), Biotin (100 μg), Thiamine HCl (1000 μg), Calcium-Pantothenic Acid (2000 μg), and Nicotinamide (2000 μg) (based on 1 L of distilled water)

<Production Medium (pH 7.0)>

Glucose (100 g), Ammonium Acetate (7.1 g) (with or without addition), $(NH_4)_2SO_4$ (40 g), Soybean Protein (2.5 g), Corn Steep Solid (5 g), Urea (3 g), $KH_2PO_4$ (1 g), $MgSO_4 \cdot 7H_2O$ (0.5 g), Biotin (100 μg), Thiamine HCl (1000 μg), Calcium-Pantothenic Acid (2000 μg), Nicotinamide (3000 μg), and $CaCO_3$ (30 g) (based on 1 L of distilled water)

As shown in FIG. 1*a*, the KCCM11016P::Ppta_ackA(Tn) strain produced acetate in a medium without acetate while consuming glucose, and consumed acetate after consuming all glucose, unlike the parent strain KCCM11016P. From this result, it was confirmed that acetate kinase is involved in the production of acetate. Additionally, it was observed that the culture rate was delayed upon production of acetate.

However, as shown in FIG. 1*b*, the KCCM11016P::Ppta_ackA(Tn) strain showed a feature of more rapid acetate consumption at the initial stage of culture when cultured in a medium with acetate, compared to that of the KCCM11016P strain (control group), and as a result, the lag phase in the growth of the strain was significantly reduced compared to that of the control group. The KCCM11016P::pta(Tn) strain did not show a significant difference in acetate consumption rate compared to that of the control group. However, it was confirmed that the KCCM11016P::pta-ackA(Tn) strain, in which two genes were both introduced in the form of an operon, showed a slight increase in the acetate consumption rate compared to that of the KCCM11016P::Ppta_ackA(Tn) strain, in which only the ackA gene was introduced.

From the above results, it was confirmed that acetate kinase, which is encoded by ackA gene, is the main enzyme in the production or activation of acetate, and it is involved in the production of acetate when acetate is not present in the medium, whereas when acetate is present in the medium it is used in the acetate activation pathway. Additionally, it was confirmed that the overexpression of ackA may significantly increase the acetate-utilizing ability due to the enhancement of the activation pathway while reducing the growth inhibition, thereby possibly reducing the lag phase.

Example 3

Preparation of a Strain Overexpressing ackA Gene by Strong Promoter and Confirmation of the Effect Thereof In order to reconfirm the acetate-utilizing ability and its effect by the overexpression of the ackA gene, an attempt was made to induce the expression of ackA gene being further inserted using lysCP1 promoter (Korean Patent No. 10-0930203), which is a strong promoter reported previously. The primers used in Examples of the present disclosure are shown in Table 2 below.

A vector for inserting a chromosome was prepared using the pDZTn vector described in Example 1 as the basic vector. The primers (SEQ ID NOS: 6 and 7) for amplifying the lysCP1 promoter region were synthesized based on the polynucleotide sequences reported previously, and a DNA segment with a size of about 450 bp was obtained by PCR using the chromosomal DNA of the *Corynebacterium glutamicum* KCCM11016P-lysCP1 (Korean Patent No. 10-0930203) as a template. In particular, PCR was performed under the following conditions: denaturation at 94° C. for 5 min; 30 cycles of denaturation at 94° C. for 30 sec, annealing at 56° C. for 30 sec, and polymerization at 72° C. for 30 sec; and polymerization at 72° C. for 7 min.

TABLE 2

| Primer | Sequence | SEQ ID NO |
|---|---|---|
| lysCP1 primer 1 | gttcctcgagtactgtttgtaagaaatatg | 6 |
| lysCP1 primer 2 | atgccatatgctttgtgcacctttcgatct | 7 |

Figure 2:
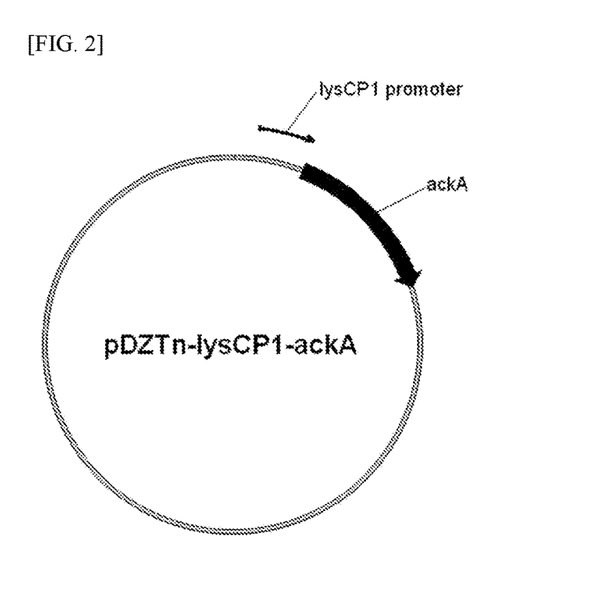
FIG. 2 shows a schematic diagram of pDZTn-lysCP1-ackA, a vector for overexpressing ackA by LysCP1 promoter, which is a strong promoter.

The PCR-amplified DNA fragments were treated with restriction enzymes, XhoI and NdeI, to obtain DNA segments, respectively. The thus-obtained DNA fragments were ligated into pDZTN vector having XhoI and SpeI ends along with the DNA fragments around the ORF region of the ackA gene having NdeI and SpeI ends prepared in Example 1, transformed into *E. coli* DH5a, and plated on LB solid medium containing kanamycin (25 mg/L). The colonies transformed with the vector, in which a target gene was inserted, were selected, the plasmid was obtained by the conventionally known plasmid extraction method, and the thus-obtained plasmid was named as pDZTN-lysCP1_ackA (FIG. 2).

The thus-prepared vector pDZTN-lysCP1_ackA was transformed into *Corynebacterium glutamicum* KCCM11016P, which produces L-lysine, by homologous recombination. Then, the colonies, in which the pDZTN-lysCP1_ackA was integrated into the chromosome by PCR, were selectively isolated, and named as KCCM11016P::lysCP1_ackA(Tn).

Figure 3:
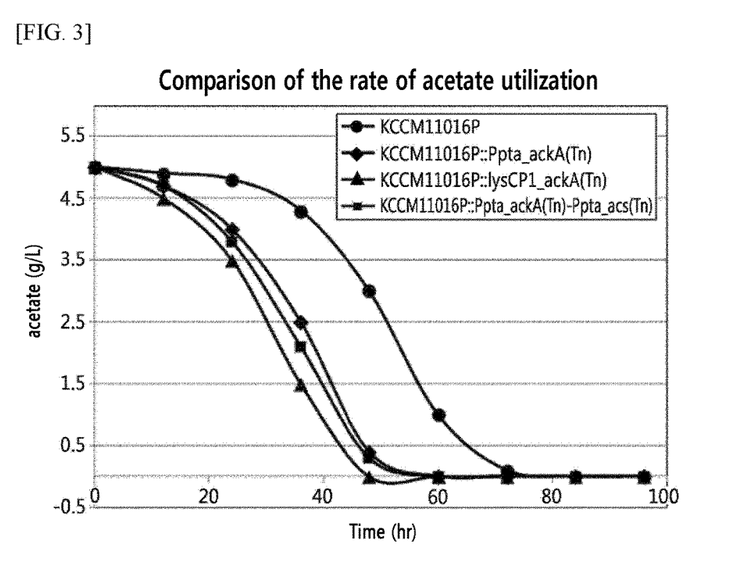
FIG. 3 shows a graph illustrating the analysis of acetate-utilizing abilities of KCCM11016P (a control strain) and a modified KCCM11016P (a modified strain introduced with pta, pta-ackA, and acs).

The KCCM11016P::lysCP1_ackA(Tn) strain, the KCCM11016P::Ppta_ackA(Tn) strain, and the KCCM11016P strain (control group) were cultured in the same manner as in Example 2, and the amount of acetate remaining in the cultured media was analyzed every 12 hours. The results are shown in FIG. 3.

As a result, the KCCM11016P::Ppta_ackA(Tn) strain showed improved acetate-utilizing ability compared to that of the control group, as shown in the result of Example 2. Additionally, it was confirmed that the KCCM11016P::lysCP1_ackA(Tn) strain showed an increased acetate consumption rate compared to that of the KCCM11016P::Ppta_ackA(Tn) strain.

The above result indicates that the acetate-utilizing rate increases as the amount of the ackA gene expression increases, and from the result, it was reconfirmed that the overexpression of the ackA gene is the major cause of increasing the acetate-utilizing ability.

Example 4

Analysis of Lysine-producing Ability of the Strain Overexpressing ackA Gene

In order to confirm the lysine-producing ability of the *Corynebacterium glutamicum* KCCM11016P::lysCP1_ackA(Tn) strain prepared in Example 3, the *Corynebacterium glutamicum* KCCM11016P::lysCP1_ackA(Tn) strain was cultured along with the KCCM11016P strain (control group) in the same manner as in Example 2. Upon completion of the culture, the L-lysine concentration was analyzed by HPLC and the results are shown in Table 3 below.

TABLE 3

| Medium Conditions | Strain No. | | Primary | | | Secondary | | | Tertiary | | |
|---|---|---|---|---|---|---|---|---|---|---|---|
| | | | Lysine Conc. (g/L) | Lysine Yield (%) | Mean (%) | Lysine Conc. (g/L) | Lysine Yield (%) | Mean (%) | Lysine Conc. (g/L) | Lysine Yield (%) | Mean (%) |
| Without Acetate | KCCM11016P | 1 | 42.3 | 42.3 | 42.2 | 42.4 | 42.4 | 42.4 | 41.0 | 41.5 | 42.0 |
| | | 2 | 42.0 | 42.0 | | 43.0 | 43.0 | | 42.1 | 42.1 | |
| | | 3 | 42.4 | 42.4 | | 41.9 | 41.9 | | 42.3 | 42.3 | |
| | KCCM11016P::lysCP1_ackA(Tn) | 1 | 43.0 | 43.0 | 42.6 | 42.2 | 42.2 | 42.3 | 42.3 | 42.3 | 42.4 |
| | | 2 | 42.9 | 42.9 | | 42.7 | 42.7 | | 42.5 | 42.5 | |
| | | 3 | 41.9 | 41.9 | | 42.1 | 42.1 | | 42.4 | 42.4 | |
| With Acetate | KCCM11016P | 1 | 43.5 | 41.4 | 41.4 | 43.4 | 41.3 | 41.7 | 44.5 | 42.4 | 41.9 |
| | | 2 | 44.1 | 42.0 | | 44.0 | 41.9 | | 43.9 | 41.8 | |
| | | 3 | 42.9 | 40.9 | | 43.8 | 41.7 | | 43.5 | 41.4 | |
| | KCCM11016P::lysCP1_ackA(Tn) | 1 | 49.5 | 47.1 | 46.8 | 49.5 | 47.1 | 47.0 | 48.8 | 46.5 | 47.1 |
| | | 2 | 49.0 | 46.7 | | 48.9 | 46.6 | | 50.2 | 47.8 | |
| | | 3 | 48.9 | 46.6 | | 49.7 | 47.3 | | 49.5 | 47.1 | |

As a result, when the strains were cultured using glucose as the only carbon source without acetate addition, the KCCM11016P::lysCP1_ackA(Tn) strain showed the same level of lysine-producing ability as that of the control group, as shown in Table 3. However, it was confirmed that when the strains were cultured in acetate-containing media, the KCCM11016P::lysCP1_ackA(Tn) strain showed an average increase of 12% in the lysine yield (total carbon source yield=lysine concentration/(added amount of (glucose+acetate)) compared to that of the control group.

The above results support that the enhancement of the acetate activation pathway not only increases the acetate-utilizing ability but also the L-lysine-producing ability. Additionally, these results suggest that, when acetate is used as a carbon source, the use of the strain with enhanced ackA gene of the present disclosure can produce lysine in high yield while reducing the culture time without inhibition of cell growth.

Under these circumstances, the present inventors named the KCCM11016P::lysCP1_ackA(Tn) strain with increased acetate-utilizing ability and L-lysine-producing ability as *Corynebacterium glutamicum* "CA01-2278" deposited in the Korean Culture Center of Microorganisms (KCCM) under the deposition number KCCM11480P.

Example 5

Preparation of a Strain Introduced with acs Gene and Analysis of the Effect of the Strain In order to insert the acetate activation pathway derived from *Escherichia* into the chromosome of *Corynebacterium*, a vector for inserting chromosome was prepared using the pDZTn vector mentioned in Example 1 as the basic vector, after obtaining the acs gene (SEQ ID NO: 11), which is known as the acetate activation pathway derived from *Escherichia*. The expression was induced by operably linking the promoter of the pta-ackA gene derived from *Corynebacterium* into the upstream region of the initiation codon of the acs gene. The primers used in the present disclosure are shown in Table 4 below.

The primers (SEQ ID NOS: 8 and 9) for amplifying the acs gene region were synthesized based on the polynucleotide sequences reported previously, and the ORF region of the acs gene with a size of about 2000 bp was amplified by PCR using the chromosome of *E. coli* W (ATCC9637) strain as a template. In particular, PCR was performed under the following conditions: denaturation at 94° C. for 5 min; 30 cycles of denaturation at 94° C. for 30 sec, annealing at 56° C. for 30 sec, and polymerization at 72° C. for 2 min; and polymerization at 72° C. for 7 min.

TABLE 4

| Primer | Sequence | SEQ ID NO |
|---|---|---|
| acs primer 1 | atcgcatatgagccaaattcacaaacac | 8 |
| acs primer 2 | atcgactagtttatgggagaaggttaac gctcgg | 9 |

The PCR-amplified DNA fragments were treated with restriction enzymes, SpeI and NdeI, along with the DNA fragments of the promoter of pta_ackA operon, which were obtained in Example 5, to obtain each DNA segment. The thus-obtained DNA segments were ligated into pDZTN vector having a SpeI end, transformed into *E. coli* DH5α, and plated on LB solid medium containing kanamycin (25 mg/L). The colonies transformed with the vector, in which a target gene was inserted, were selected, the plasmid was obtained by the conventionally known plasmid extraction method, and the thus-obtained plasmid was named as pDZTN-Ppta-acs.

The thus-prepared vector was transformed into *Corynebacterium glutamicum* KCCM11016P::Ppta_ackA(Tn) prepared in Example 2 by electric pulse method, and the strains in which the acs gene was inserted into the chromosome by homologous recombination were selected. In particular, those colonies in which the acs gene was inserted into a transposon different from the transposon in which the Ppta_ackA gene was previously inserted were selectively isolated by PCR and named as KCCM11016P::Ppta_ackA(Tn)-Ppta_acs(Tn).

The KCCM11016P::Ppta_ackA(Tn)-Ppta_acs(Tn) strain and the KCCM11016P::Ppta_ackA(Tn) strain (control group) were cultured in the same manner as in Example 2, and the amount of acetate remaining in the cultured media was analyzed every 12 hours.

As a result, it was confirmed that the KCCM11016P::Ppta_ackA(Tn)-Ppta_acs(Tn) strain showed a slight increase in the acetate consumption rate compared to that of the control group (FIG. 3).

The result suggests that not only the overexpression of the ackA gene but also the introduction of the acs gene, which is a foreign gene derived from *Escherichia*, in a microorganism of the genus *Corynebacterium* can increase the acetate consumption rate and the L-lysine-producing ability.

Example 7

Comparison of L-lysine-Producing Ability of Strains, which Overexpress ackA Gene, Derived from L-lysine-Producing Strain In order to confirm the effect of enhancing lysine production by the ackA-overexpressing strains, the L-lysine-producing ability of various lysine-producing strains derived from *Corynebacterium* was compared.

The ackA gene was introduced into three representative lysine-producing strains, *Corynebacterium glutamicum* KCCM10770P (Korean Patent No. 10-0924065), KCCM11347P (the microorganism was originally disclosed as KFCC10750 and re-deposited to an international depositary authority under the Budapest Treaty and assigned the Accession No. KCCM11347P; Korean Patent No.10-0073610), and CJ3P (Binder et al. *Genome Biology* 2012, 13: R40), and their L-lysine-producing abilities were compared.

The vector pDZTN-lysCP1_ackA prepared in Example 3 was transformed into *Corynebacterium glutamicum* KCCM10770P, KCCM11347P, and CJ3P, respectively on the chromosome by homologous recombination. Then, the colonies were selectively isolated by PCR, and each of the strains was named as KCCM10770P::lysCP1_ackA(Tn), KCCM11347P::lysCP1_ackA(Tn), and CJ3P::lysCP1_ackA(Tn), respectively.

For the comparison of the lysine-producing ability of the above strains, the strains were cultured along with each of the control groups in the same manner as in Example 2. Upon completion of the culture, the L-lysine concentration was analyzed by HPLC and the results are shown in Table 5 below.

TABLE 5

| | | Primary | | Secondary | | Tertiary | |
|---|---|---|---|---|---|---|---|
| Strain No. | | Lysine Yield (%) | Mean (%) | Lysine Yield (%) | Mean (%) | Lysine Yield (%) | Mean (%) |
| KCCM10770P | 1 | 47.0 | 47.0 | 47.4 | 47.2 | 47.5 | 46.9 |
| | 2 | 46.4 | | 47.3 | | 46.8 | |
| | 3 | 47.5 | | 46.9 | | 46.5 | |

TABLE 5-continued

| Strain No. | | Primary Lysine Yield (%) | Primary Mean (%) | Secondary Lysine Yield (%) | Secondary Mean (%) | Tertiary Lysine Yield (%) | Tertiary Mean (%) |
|---|---|---|---|---|---|---|---|
| KCCM10770P::lysCP1_ackA(Tn) | 1 | 52.6 | 52.3 | 51.4 | 52.5 | 52.4 | 52.2 |
| | 2 | 52.4 | | 53.1 | | 52.9 | |
| | 3 | 51.9 | | 52.9 | | 51.2 | |
| KCCM11347P | 1 | 38.0 | 38.0 | 37.9 | 38.2 | 38.9 | 38.7 |
| | 2 | 37.4 | | 37.9 | | 38.7 | |
| | 3 | 38.5 | | 38.7 | | 38.4 | |
| KCCM11347P::lysCP1_ackA(Tn) | 1 | 42.7 | 42.4 | 42.4 | 42.5 | 42.2 | 42.1 |
| | 2 | 42.0 | | 43.1 | | 42.3 | |
| | 3 | 42.4 | | 41.9 | | 41.9 | |
| CJ3P | 1 | 8.0 | 8.4 | 7.5 | 7.9 | 7.8 | 8.2 |
| | 2 | 8.2 | | 8.1 | | 8.3 | |
| | 3 | 9.1 | | 8.0 | | 8.4 | |
| CJ3P::lysCP1_ackA(Tn) | 1 | 9.1 | 9.1 | 8.5 | 8.9 | 9.2 | 9.0 |
| | 2 | 8.9 | | 8.9 | | 9.5 | |
| | 3 | 9.2 | | 9.2 | | 8.4 | |

As a result, as shown in Table 5, all of the ackA-overexpressing strains derived from a lysine-producing strain showed an increase in L-lysine-producing ability. The KCCM10770P::lysCP1_ackA(Tn) strain showed an increase of about 11% in lysine concentration compared to that of the KCCM10770P strain (control group). The KCCM11347P::lysCP1_ackA(Tn) strain showed an increase of about 10% in lysine concentration compared to that of the KCCM11347P strain (control group). The CJ3P::lysCP1_ackA(Tn) strain showed an increase of about 11% in lysine concentration compared to that of the CJ3P strain (control group).

Accordingly, from the above results, it was confirmed that the increase in the activity of acetate kinase in various types of L-lysine-producing strains derived from *Corynebacterium glutamicum* has the effect of increasing the L-lysine-producing ability.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

The invention claimed is:

1. A modified microorganism of the genus *Corynebacterium* having increased L-lysine productivity compared to an unmodified microorganism, wherein the enzyme activity of acetate kinase (ackA) is increased by over-expression of ackA gene in the microorganism compared to its endogenous activity and the acetate kinase comprises the amino acid sequence of SEQ ID NO: 12.

2. The microorganism according to claim 1, wherein, additionally, (i) enzyme activity of phosphotransacetylase is increased compared to its endogenous activity; (ii) enzyme activity of acetyl-CoA synthetase is introduced or increased; or (iii) enzyme activity of phosphotransacetylase is increased compared to its endogenous activity and enzyme activity of acetyl-CoA synthetase is introduced or increased.

3. The microorganism according to claim 2, wherein the phosphotransacetylase comprises the amino acid sequence of SEQ ID NO: 13.

4. The microorganism according to claim 2, wherein the acetyl-CoA synthetase comprises the amino acid sequence of SEQ ID NO: 14.

5. The microorganism according to claim 1, wherein the microorganism of the genus *Corynebacterium* is *Corynebacterium glutamicum*.

6. A method for producing L-lysine, comprising:
(i) culturing the microorganism of the genus *Corynebacterium* of claim 1 having increased L-lysine productivity compared to an unmodified microorganism, wherein enzyme activity of acetate kinase is increased compared to its endogenous activity; and
(ii) recovering L-lysine from the cultured microorganism or the cultured medium.

* * * * *

SEQUENCE LISTING

```
<160> NUMBER OF SEQ ID NOS: 14

<210> SEQ ID NO 1
<211> LENGTH: 28
<212> TYPE: DNA
<213> ORGANISM: Artificial Sequence
<220> FEATURE:
<223> OTHER INFORMATION: ackA primer 1

<400> SEQUENCE: 1
atcgcatatg gcattggcac ttgttttg                                        28

<210> SEQ ID NO 2
<211> LENGTH: 34
<212> TYPE: DNA
<213> ORGANISM: Artificial Sequence
<220> FEATURE:
<223> OTHER INFORMATION: ackA primer 2

<400> SEQUENCE: 2
atcgactagt atccgtgcag tttcacccct taaa                                 34

<210> SEQ ID NO 3
<211> LENGTH: 34
<212> TYPE: DNA
<213> ORGANISM: Artificial Sequence
<220> FEATURE:
```

```
<223> OTHER INFORMATION: Ppta primer 1

<400> SEQUENCE: 3
atcgactagt ctttgctggg gtcagatttg tcac                                34

<210> SEQ ID NO 4
<211> LENGTH: 31
<212> TYPE: DNA
<213> ORGANISM: Artificial Sequence
<220> FEATURE:
<223> OTHER INFORMATION: Ppta primer 2

<400> SEQUENCE: 4
atcgcatatg tcgcctttct aatttcagcc t                                   31

<210> SEQ ID NO 5
<211> LENGTH: 31
<212> TYPE: DNA
<213> ORGANISM: Artificial Sequence
<220> FEATURE:
<223> OTHER INFORMATION: pta primer

<400> SEQUENCE: 5
atcgactagt ggcagagttt tcggggttga c                                   31

<210> SEQ ID NO 6
<211> LENGTH: 30
<212> TYPE: DNA
<213> ORGANISM: Artificial Sequence
<220> FEATURE:
<223> OTHER INFORMATION: lysCP1 primer 1

<400> SEQUENCE: 6
gttcctcgag tactgtttgt aagaaatatg                                     30

<210> SEQ ID NO 7
<211> LENGTH: 30
<212> TYPE: DNA
<213> ORGANISM: Artificial Sequence
<220> FEATURE:
<223> OTHER INFORMATION: lysCP1 primer 2

<400> SEQUENCE: 7
atgccatatg ctttgtgcac ctttcgatct                                     30

<210> SEQ ID NO 8
<211> LENGTH: 28
<212> TYPE: DNA
<213> ORGANISM: Artificial Sequence
<220> FEATURE:
<223> OTHER INFORMATION: acs primer 1

<400> SEQUENCE: 8
atcgcatatg agccaaattc acaaacac                                       28

<210> SEQ ID NO 9
<211> LENGTH: 34
<212> TYPE: DNA
<213> ORGANISM: Artificial Sequence
<220> FEATURE:
<223> OTHER INFORMATION: acs primer 2

<400> SEQUENCE: 9
atcgactagt ttatgggaga aggttaacgc tcgg                                34
```

<210> SEQ ID NO 10
<211> LENGTH: 3007
<212> TYPE: DNA
<213> ORGANISM: Artificial Sequence
<220> FEATURE:
<223> OTHER INFORMATION: PTA-ACKA

<400> SEQUENCE: 10

| | | | | | |
|---|---|---|---|---|---|
| ctttgctggg | gtcagatttg | tcacgctgcg | cgctttcata | gaccccatta | atgggggtg | 60 |
| aagagctgta | aagtaccgct | aaaaactttg | caaagggtgc | ttcgcaactt | gtaaccgctc | 120 |
| cgtattgttt | tctacggcaa | taagcatttg | tgctgctcaa | agcgtggaat | tgagatcggt | 180 |
| ttgaaaatta | caaataaaa | ctttgcaaac | cgggctgtac | gcaaggcgga | cgaacgctaa | 240 |
| actatgtaag | aaatcacaac | ctcccctcat | tagtgccagg | aggcacaagc | ctgaagtgtc | 300 |
| atcaatgaga | aggttcaggc | tgaaattaga | aaggcgatgt | atgtctgaca | caccgacctc | 360 |
| agctctgatc | accacggtca | accgcagctt | cgatggattc | gatttggaag | aagtagcagc | 420 |
| agaccttgga | gttcggctca | cctacctgcc | cgacgaagaa | ctagaagtat | ccaaagttct | 480 |
| cgcggcggac | ctcctcgctg | aggggccagc | tctcatcatc | ggtgtaggaa | acacgttttt | 540 |
| cgacgcccag | gtcgccgctg | ccctcggcgt | cccagtgcta | ctgctggtag | acaagcaagg | 600 |
| caagcacgtt | gctcttgctc | gcacccaggt | aaacaatgcc | ggcgcagttg | ttgcagcagc | 660 |
| atttaccgct | gaacaagagc | caatgccgga | taagctgcgc | aaggctgtgc | gcaaccacag | 720 |
| caacctcgaa | ccagtcatga | gcgccgaact | cttttgaaaac | tggctgctca | agcgcgcacg | 780 |
| cgcagagcac | tcccacattg | tgctgccaga | aggtgacgac | gaccgcatct | tgatggctgc | 840 |
| ccaccagctg | cttgatcaag | acatctgtga | catcacgatc | ctgggcgatc | cagtaaagat | 900 |
| caaggagcgc | gctaccgaac | ttggcctgca | ccttaacact | gcatacctgg | tcaatccgct | 960 |
| gacagatcct | cgcctggagg | aattcgccga | acaattcgcg | gagctgcgca | agtcaaagag | 1020 |
| cgtcactatc | gatgaagccc | gcgaaatcat | gaaggatatt | tcctacttcg | gcaccatgat | 1080 |
| ggtccacaac | ggcgacgccg | acggaatggt | atccggtgca | gcaaacacca | ccgcacacac | 1140 |
| cattaagcca | agcttccaga | tcatcaaaac | tgttccagaa | gcatccgtcg | tttcttccat | 1200 |
| cttcctcatg | gtgctgcgcg | ggcgactgtg | gcattcggc | gactgtgctg | ttaacccgaa | 1260 |
| cccaactgct | gaacagcttg | gtgaaatcgc | cgttgtgtca | gcaaaaactg | cagcacaatt | 1320 |
| tggcattgat | cctcgcgtag | ccatcttgtc | ctactccact | ggcaactccg | gcggaggctc | 1380 |
| agatgtggat | cgcgccatcg | acgctcttgc | agaagcacgc | cgacttaacc | cagaactatg | 1440 |
| cgtcgatgga | ccacttcagt | tcgacgccgc | cgtcgaccg | ggtgtggcgc | gcaagaagat | 1500 |
| gccagactct | gacgtcgctg | gccaggcaaa | tgtgtttatc | ttccctgacc | tggaagccgg | 1560 |
| aaacatcggc | tacaaaactg | cacaacgcac | cggtcacgcc | ctggcagttg | gtccgattct | 1620 |
| gcagggccta | aacaaaccag | tcaacgacct | ttcccgtggc | gcaacagtcc | ctgacatcgt | 1680 |
| caacacagta | gccatcacag | caattcaggc | aggaggacgc | agctaatggc | attggcactt | 1740 |
| gttttgaact | ccggttcatc | ttccatcaaa | ttccagctgg | tcaacccga | aaactctgcc | 1800 |
| atcgacgagc | catatgtttc | tggtcttgtg | gagcagattg | gtgagccaa | cggccgcatc | 1860 |
| gtactcaaaa | tagagggtga | aaaatatacc | ctagagacac | ccatcgcaga | tcactccgaa | 1920 |
| ggcctaaacc | tggcgttcga | tctcatggac | cagcacaact | gtggtccttc | ccaactggaa | 1980 |
| atcaccgcag | ttgacaccg | cgtggtccac | ggcggaatct | tgttctccgc | accggaactt | 2040 |
| atcactgatg | aaatcgtgga | aatgatccgc | gatctcattc | cactcgcacc | actgcacaac | 2100 |

-continued

```
cctgcaaacg ttgacggcat tgatgttgct cgaaaaattc tccccgatgt cccacacgta    2160
gctgtctttg acaccggttt cttccactca cttccaccag cagctgcgct gtatgccatc    2220
aacaaggatg tcgcagctga acacggaatc aggcgctatg gtttccacgg cacctcccat    2280
gaatttgtgt ccaagcgcgt ggtggaaatt ctggaaaagc ccaccgaaga catcaacacc    2340
atcaccttcc acctgggcaa cggcgcatcc atggctgctg ttcaaggtgg ccgtgcggta    2400
gatacttcca tgggtatgac acctctcgcg ggccttgtca tgggtacccg aagcggtgac    2460
attgatccag gtatcgtctt ccacctttcc cgcaccgctg gcatgagcat cgatgagatc    2520
gataatctgc tgaacaaaaa gtcgggtgta aagggacttt ccggtgttaa tgatttccgt    2580
gaactgcggg aaatgatcga caacaatgat caagatgcct ggtccgcgta caacatttac    2640
atacaccaac tccgccgcta cctcggttcc tacatggtgg cactgggacg ggtagacacc    2700
atcgtgttca ccgccggtgt cggtgaaaat gcccagtttg tccgtgagga tgccttggca    2760
ggtttggaaa tgtacggaat tgagatcgat ccagagcgta acgcattgcc aaacgatggt    2820
cctcgattga tttccaccga tgcctccaag gtgaaggtgt tgttattcc aactaatgaa     2880
gagttagcta tcgctaggta cgcggtgaag ttcgcttagc tctcctggtt aggatccacc    2940
acaaatcgct ctgatcagcg gttttgtggt ggattttttgc gttttttaagg ggtgaaactg   3000
cacggat                                                              3007
```

```
<210> SEQ ID NO 11
<211> LENGTH: 2110
<212> TYPE: DNA
<213> ORGANISM: Escherichia coli

<400> SEQUENCE: 11
```

```
atgagccaaa ttcacaaaca caccattcct gccaacatcg cagaccgttg cctgataaac      60
cctcagcagt acgaggcgat gtatcaacaa tctattaacg tacctgatac cttctggggc     120
gaacagggaa aaattcttga ctggatcaaa ccttaccaga aggtgaaaaa cacctccttt     180
gccccccggta atgtgtccat taaatggtac gaggacggca cgctgaatct ggcggcaaac    240
tgccttgacc gccatctgca agaaaacggc gatcgtaccg ccatcatctg gaaggcgac      300
gacgccagcc agagcaaaca tatcagctat aaagagctgc accgcgacgt ctgccgcttc    360
gccaataccc tgctcgagct gggcattaaa aaaggtgatg tggtggcgat ttatatgccg    420
atggtgccgg aagccgcggt tgcgatgctg gcctgcgccc gcattggcgc ggtgcattcg    480
gtgatttttcg cggcttctc gccggaagcc gttgccgggc gcattattga ttccaactca   540
cgactggtga tcacttccga cgaaggtgtg cgtgccgggc gcagtattcc gctgaagaaa   600
aacgttgatg acgcgctgaa aaacccgaac gtcaccagcg tagagcatgt ggtggtactg   660
aagcgtactg gcgggaaaat tgactggcag gaagggcgcg acctgtggtg gcacgaccctg  720
gttgagcaag cgagcgatca gcaccaggcg gaagagatga acgccgaaga tccgctgttt   780
attctctaca cctccggttc taccggtaag ccaaaaggtg tgctgcatac taccggcggt   840
tatctggtgt acgcggcgct gaccttttaaa tatgtctttg attatcatcc gggtgatatc   900
tactggtgca ccgccgatgt gggctggtg accggacaca gttacttgct gtacggcccg    960
ctggcctgcg gtgcgaccac gctgatgttt gaaggcgtac ccaactggcc gacgcctgcc   1020
cgtatgcgc aggtggtgga caagcatcag gtcaatattc tctataccgc acccacggcg   1080
atccgcgcgc tgatgcgga aggcgataaa gcgatcgaag caccgaccg ttcgtcgctg    1140
cgcattctcg gttccgtggg cgagccaatt aacccggaag cgtgggagtg gtactggaaa    1200
```

-continued

```
aaaatcggca acgagaaatg tccggtggtc gatacctggt ggcagaccga aaccggcggt    1260
ttcatgatca ccccgctgcc tggcgctacc gagctgaaag ccggttcggc aacacgtccg    1320
ttcttcggcg tgcaaccggc gctggtcgat aacgaaggta acccgctgga gggggccacc    1380
gaaggtagcc tggtaatcac cgactcctgg ccgggtcagg cgcgtacgct gtttggcgat    1440
cacgaacgtt ttgaacagac ctacttctcc accttcaaaa atatgtattt cagcggcgac    1500
ggcgcgcgtc gcgatgaaga tggctattac tggataaccg gcgtgtgga cgacgtgctg    1560
aacgtctccg gtcaccgtct ggggacggca gagattgagt cggcgctggt ggcgcatccg    1620
aagattgccg aagccgccgt agtaggtatt ccgcacaata ttaaaggtca ggcgatctac    1680
gcctacgtca cgcttaatca cggggaggaa ccgtcaccag aactgtacgc agaagtccgc    1740
aactgggtgc gtaaagagat tggcccgctg gcgacgccag acgtgctgca ctggaccgac    1800
tccctgccta aacccgctc cggcaaaatt atgcgccgta ttctgcgcaa aattgcggcg    1860
ggcgatacca gcaacctggg cgatacctcg acgcttgccg atcctggcgt agtcgagaag    1920
ctgcttgaag agaagcaggc tatcgcgatg ccatcgtaac ccacaattgc ccgatgcgag    1980
tcggtaacgg tttgtaggcc tgataagacg cgacagcgtc gcatcaggca ttgattgccg    2040
gatgcggcgt aaacgcctta tccggcctac attcggcaag ggttacccga gcgttaacct    2100
tctcccataa                                                           2110
```

<210> SEQ ID NO 12
<211> LENGTH: 397
<212> TYPE: PRT
<213> ORGANISM: Corynebacterium glutamicum

<400> SEQUENCE: 12

```
Met Ala Leu Ala Leu Val Leu Asn Ser Gly Ser Ser Ile Lys Phe
 1               5                  10                  15

Gln Leu Val Asn Pro Glu Asn Ser Ala Ile Asp Glu Pro Tyr Val Ser
             20                  25                  30

Gly Leu Val Glu Gln Ile Gly Glu Pro Asn Gly Arg Ile Val Leu Lys
         35                  40                  45

Ile Glu Gly Glu Lys Tyr Thr Leu Glu Thr Pro Ile Ala Asp His Ser
     50                  55                  60

Glu Gly Leu Asn Leu Ala Phe Asp Leu Met Asp Gln His Asn Cys Gly
 65                  70                  75                  80

Pro Ser Gln Leu Glu Ile Thr Ala Val Gly His Arg Val His Gly
             85                  90                  95

Gly Ile Leu Phe Ser Ala Pro Glu Leu Ile Thr Asp Glu Ile Val Glu
        100                 105                 110

Met Ile Arg Asp Leu Ile Pro Leu Ala Pro Leu His Asn Pro Ala Asn
        115                 120                 125

Val Asp Gly Ile Asp Val Ala Arg Lys Ile Leu Pro Asp Val Pro His
    130                 135                 140

Val Ala Val Phe Asp Thr Gly Phe Phe His Ser Leu Pro Pro Ala Ala
145                 150                 155                 160

Ala Leu Tyr Ala Ile Asn Lys Asp Val Ala Ala Glu His Gly Ile Arg
                165                 170                 175

Arg Tyr Gly Phe His Gly Thr Ser His Glu Phe Val Ser Lys Arg Val
            180                 185                 190

Val Glu Ile Leu Glu Lys Pro Thr Glu Asp Ile Asn Thr Ile Thr Phe
        195                 200                 205
```

```
His Leu Gly Asn Gly Ala Ser Met Ala Ala Val Gln Gly Gly Arg Ala
    210                 215                 220

Val Asp Thr Ser Met Gly Met Thr Pro Leu Ala Gly Leu Val Met Gly
225                 230                 235                 240

Thr Arg Ser Gly Asp Ile Asp Pro Gly Ile Val Phe His Leu Ser Arg
                245                 250                 255

Thr Ala Gly Met Ser Ile Asp Glu Ile Asp Asn Leu Leu Asn Lys Lys
            260                 265                 270

Ser Gly Val Lys Gly Leu Ser Gly Val Asn Asp Phe Arg Glu Leu Arg
        275                 280                 285

Glu Met Ile Asp Asn Asn Asp Gln Asp Ala Trp Ser Ala Tyr Asn Ile
290                 295                 300

Tyr Ile His Gln Leu Arg Arg Tyr Leu Gly Ser Tyr Met Val Ala Leu
305                 310                 315                 320

Gly Arg Val Asp Thr Ile Val Phe Thr Ala Gly Val Gly Glu Asn Ala
                325                 330                 335

Gln Phe Val Arg Glu Asp Ala Leu Ala Gly Leu Glu Met Tyr Gly Ile
            340                 345                 350

Glu Ile Asp Pro Glu Arg Asn Ala Leu Pro Asn Asp Gly Pro Arg Leu
        355                 360                 365

Ile Ser Thr Asp Ala Ser Lys Val Lys Val Phe Val Ile Pro Thr Asn
370                 375                 380

Glu Glu Leu Ala Ile Ala Arg Tyr Ala Val Lys Phe Ala
385                 390                 395

<210> SEQ ID NO 13
<211> LENGTH: 461
<212> TYPE: PRT
<213> ORGANISM: Corynebacterium glutamicum

<400> SEQUENCE: 13

Met Ser Asp Thr Pro Thr Ser Ala Leu Ile Thr Thr Val Asn Arg Ser
1               5                   10                  15

Phe Asp Gly Phe Asp Leu Glu Glu Val Ala Ala Asp Leu Gly Val Arg
            20                  25                  30

Leu Thr Tyr Leu Pro Asp Glu Glu Leu Glu Val Ser Lys Val Leu Ala
        35                  40                  45

Ala Asp Leu Leu Ala Glu Gly Pro Ala Leu Ile Ile Gly Val Gly Asn
    50                  55                  60

Thr Phe Phe Asp Ala Gln Val Ala Ala Leu Gly Val Pro Val Leu
65                  70                  75                  80

Leu Leu Val Asp Lys Gln Gly Lys His Val Ala Leu Ala Arg Thr Gln
                85                  90                  95

Val Asn Asn Ala Gly Ala Val Ala Ala Ala Phe Thr Ala Glu Gln
            100                 105                 110

Glu Pro Met Pro Asp Lys Leu Arg Lys Ala Val Arg Asn His Ser Asn
        115                 120                 125

Leu Glu Pro Val Met Ser Ala Glu Leu Phe Glu Asn Trp Leu Leu Lys
    130                 135                 140

Arg Ala Arg Ala Glu His Ser His Ile Val Leu Pro Glu Gly Asp Asp
145                 150                 155                 160

Asp Arg Ile Leu Met Ala Ala His Gln Leu Leu Asp Gln Asp Ile Cys
                165                 170                 175

Asp Ile Thr Ile Leu Gly Asp Pro Val Lys Ile Lys Glu Arg Ala Thr
```

```
            180                 185                 190
Glu Leu Gly Leu His Leu Asn Thr Ala Tyr Leu Val Asn Pro Leu Thr
        195                 200                 205

Asp Pro Arg Leu Glu Glu Phe Ala Glu Gln Phe Ala Glu Leu Arg Lys
    210                 215                 220

Ser Lys Ser Val Thr Ile Asp Glu Ala Arg Glu Ile Met Lys Asp Ile
225                 230                 235                 240

Ser Tyr Phe Gly Thr Met Met Val His Asn Gly Asp Ala Asp Gly Met
                245                 250                 255

Val Ser Gly Ala Ala Asn Thr Thr Ala His Thr Ile Lys Pro Ser Phe
            260                 265                 270

Gln Ile Ile Lys Thr Val Pro Glu Ala Ser Val Val Ser Ser Ile Phe
        275                 280                 285

Leu Met Val Leu Arg Gly Arg Leu Trp Ala Phe Gly Asp Cys Ala Val
    290                 295                 300

Asn Pro Asn Pro Thr Ala Glu Gln Leu Gly Glu Ile Ala Val Val Ser
305                 310                 315                 320

Ala Lys Thr Ala Ala Gln Phe Gly Ile Asp Pro Arg Val Ala Ile Leu
                325                 330                 335

Ser Tyr Ser Thr Gly Asn Ser Gly Gly Ser Asp Val Asp Arg Ala
            340                 345                 350

Ile Asp Ala Leu Ala Glu Ala Arg Arg Leu Asn Pro Glu Leu Cys Val
        355                 360                 365

Asp Gly Pro Leu Gln Phe Asp Ala Ala Val Asp Pro Gly Val Ala Arg
    370                 375                 380

Lys Lys Met Pro Asp Ser Asp Val Ala Gly Gln Ala Asn Val Phe Ile
385                 390                 395                 400

Phe Pro Asp Leu Glu Ala Gly Asn Ile Gly Tyr Lys Thr Ala Gln Arg
                405                 410                 415

Thr Gly His Ala Leu Ala Val Gly Pro Ile Leu Gln Gly Leu Asn Lys
            420                 425                 430

Pro Val Asn Asp Leu Ser Arg Gly Ala Thr Val Pro Asp Ile Val Asn
        435                 440                 445

Thr Val Ala Ile Thr Ala Ile Gln Ala Gly Gly Arg Ser
    450                 455                 460

<210> SEQ ID NO 14
<211> LENGTH: 652
<212> TYPE: PRT
<213> ORGANISM: Unknown
<220> FEATURE:
<223> OTHER INFORMATION: Enterobacteriaceae

<400> SEQUENCE: 14

Met Ser Gln Ile His Lys His Thr Ile Pro Ala Asn Ile Ala Asp Arg
1               5                   10                  15

Cys Leu Ile Asn Pro Gln Gln Tyr Glu Ala Met Tyr Gln Gln Ser Ile
            20                  25                  30

Asn Val Pro Asp Thr Phe Trp Gly Glu Gln Gly Lys Ile Leu Asp Trp
        35                  40                  45

Ile Lys Pro Tyr Gln Lys Val Lys Asn Thr Ser Phe Ala Pro Gly Asn
    50                  55                  60

Val Ser Ile Lys Trp Tyr Glu Asp Gly Thr Leu Asn Leu Ala Ala Asn
65                  70                  75                  80

Cys Leu Asp Arg His Leu Gln Glu Asn Gly Asp Arg Thr Ala Ile Ile
```

```
                        85                      90                      95
Trp Glu Gly Asp Asp Ala Ser Gln Ser Lys His Ile Ser Tyr Lys Glu
                    100                     105                     110

Leu His Arg Asp Val Cys Arg Phe Ala Asn Thr Leu Leu Glu Leu Gly
                    115                     120                     125

Ile Lys Lys Gly Asp Val Val Ala Ile Tyr Met Pro Met Val Pro Glu
                130                     135                     140

Ala Ala Val Ala Met Leu Ala Cys Ala Arg Ile Gly Ala Val His Ser
145                     150                     155                     160

Val Ile Phe Gly Gly Phe Ser Pro Glu Ala Val Ala Gly Arg Ile Ile
                    165                     170                     175

Asp Ser Asn Ser Arg Leu Val Ile Thr Ser Asp Glu Gly Val Arg Ala
                    180                     185                     190

Gly Arg Ser Ile Pro Leu Lys Lys Asn Val Asp Asp Ala Leu Lys Asn
                    195                     200                     205

Pro Asn Val Thr Ser Val Glu His Val Val Leu Lys Arg Thr Gly
                210                     215                     220

Gly Lys Ile Asp Trp Gln Glu Gly Arg Asp Leu Trp Trp His Asp Leu
225                     230                     235                     240

Val Glu Gln Ala Ser Asp Gln His Gln Ala Glu Met Asn Ala Glu
                    245                     250                     255

Asp Pro Leu Phe Ile Leu Tyr Thr Ser Gly Ser Thr Gly Lys Pro Lys
                    260                     265                     270

Gly Val Leu His Thr Thr Gly Gly Tyr Leu Val Tyr Ala Ala Leu Thr
                    275                     280                     285

Phe Lys Tyr Val Phe Asp Tyr His Pro Gly Asp Ile Tyr Trp Cys Thr
                    290                     295                     300

Ala Asp Val Gly Trp Val Thr Gly His Ser Tyr Leu Leu Tyr Gly Pro
305                     310                     315                     320

Leu Ala Cys Gly Ala Thr Thr Leu Met Phe Glu Gly Val Pro Asn Trp
                    325                     330                     335

Pro Thr Pro Ala Arg Met Ala Gln Val Val Asp Lys His Gln Val Asn
                    340                     345                     350

Ile Leu Tyr Thr Ala Pro Thr Ala Ile Arg Ala Leu Met Ala Glu Gly
                    355                     360                     365

Asp Lys Ala Ile Glu Gly Thr Asp Arg Ser Ser Leu Arg Ile Leu Gly
                    370                     375                     380

Ser Val Gly Glu Pro Ile Asn Pro Glu Ala Trp Glu Trp Tyr Trp Lys
385                     390                     395                     400

Lys Ile Gly Asn Glu Lys Cys Pro Val Val Asp Thr Trp Trp Gln Thr
                    405                     410                     415

Glu Thr Gly Gly Phe Met Ile Thr Pro Leu Pro Gly Ala Thr Glu Leu
                    420                     425                     430

Lys Ala Gly Ser Ala Thr Arg Pro Phe Phe Gly Val Gln Pro Ala Leu
                    435                     440                     445

Val Asp Asn Glu Gly Asn Pro Leu Glu Gly Ala Thr Glu Gly Ser Leu
                    450                     455                     460

Val Ile Thr Asp Ser Trp Pro Gly Gln Ala Arg Thr Leu Phe Gly Asp
465                     470                     475                     480

His Glu Arg Phe Glu Gln Thr Tyr Phe Ser Thr Phe Lys Asn Met Tyr
                    485                     490                     495

Phe Ser Gly Asp Gly Ala Arg Arg Asp Glu Asp Gly Tyr Tyr Trp Ile
                    500                     505                     510
```

```
Thr Gly Arg Val Asp Asp Val Leu Asn Val Ser Gly His Arg Leu Gly
        515                 520                 525

Thr Ala Glu Ile Glu Ser Ala Leu Val Ala His Pro Lys Ile Ala Glu
    530                 535                 540

Ala Ala Val Val Gly Ile Pro His Asn Ile Lys Gly Gln Ala Ile Tyr
545                 550                 555                 560

Ala Tyr Val Thr Leu Asn His Gly Glu Glu Pro Ser Pro Glu Leu Tyr
                565                 570                 575

Ala Glu Val Arg Asn Trp Val Arg Lys Glu Ile Gly Pro Leu Ala Thr
                580                 585                 590

Pro Asp Val Leu His Trp Thr Asp Ser Leu Pro Lys Thr Arg Ser Gly
        595                 600                 605

Lys Ile Met Arg Arg Ile Leu Arg Lys Ile Ala Ala Gly Asp Thr Ser
        610                 615                 620

Asn Leu Gly Asp Thr Ser Thr Leu Ala Asp Pro Gly Val Val Glu Lys
625                 630                 635                 640

Leu Leu Glu Glu Lys Gln Ala Ile Ala Met Pro Ser
                645                 650
```